United States Patent

Tarlov et al.

Patent Number: 5,942,397
Date of Patent: Aug. 24, 1999

[54] SURFACE IMMOBILIZATION OF BIOPOLYMERS

[76] Inventors: Michael J. Tarlov; Tonya M. Herne; Keith H. McKenney, all of NIST—Office of Tech. Development, Bldg. 820, Room 213, Gaithersburg, Md. 20899-0001

[21] Appl. No.: 08/988,338

[22] Filed: Dec. 10, 1997

Related U.S. Application Data

[60] Provisional application No. 60/033,042, Dec. 11, 1996.

[51] Int. Cl.[6] .................................................. C12Q 1/68
[52] U.S. Cl. ............................................. 435/6; 536/24.1
[58] Field of Search ................................. 435/6; 536/24.1

[56] References Cited

U.S. PATENT DOCUMENTS

| | | | |
|---|---|---|---|
| 5,302,509 | 4/1994 | Cheeseman | 435/6 |
| 5,445,934 | 8/1995 | Fodor et al. | 435/6 |
| 5,472,881 | 12/1995 | Beebe et al. | 436/94 |
| 5,514,501 | 5/1996 | Tarlov | 430/5 |
| 5,622,826 | 4/1997 | Varma | 435/6 |

OTHER PUBLICATIONS

Leavitt et al., "Angle–Dependent X–ray Photoelectron Spectroscopy and Atomic Force Microscopy of Sulfur–Modified DNA on Au(111)" in *J. Phys. Chem.*, (1994), 98, 8742–8746.

Lee et al., "Direct Measurement of the Forces Between Complementary Strands of DNA" in *Science*, (1994), 266, 771–773.

Okahata et al., "Hybridization of Nucleic Acids Immobilized on a Quartz Crystal Microbalance" in *J. Amer. Chem. Soc.*, (1992), 114, 8299–8300.

*Primary Examiner*—Scott W. Houtteman
*Attorney, Agent, or Firm*—Jagtiani & Associates

[57] ABSTRACT

In one embodiment, the present invention provides a biopolymer-containing monolayer comprising: thiol-derivatized biopolymers and organic thiols bound to a metal substrate. In another embodiment, the present invention provides a method for forming this biopolymer-containing monolayer. Preferably, the biopolymers are single-stranded DNA probes.

22 Claims, 6 Drawing Sheets

TABLE 1. Data obtained from radio-images of HS-ssDNA/MCH monolayers exposed to $^{32}$P-radiolabeled complement.

| Sample | Time in HS-ssDNA (min) | Time in MCH (min) | Intensity[a] Counts/cm$^2$ | $^{32}$P radiolabeled DNA[b] (molecules/cm$^2$) |
|---|---|---|---|---|
| Bare Au | 0.0 | 0.0 | 6836 ± 83 | 3.1 (±0.03) × 10$^{12}$ |
| 1[c] | 0.0 | 60 | 64±8 | 2.9 (±0.4) × 10$^{10}$ |
| 2 | 0.25 | 60 | 773±28 | 3.5 (±0.1) × 10$^{11}$ |
| 3 | 1.0 | 60 | 4018±64 | 1.8 (±0.03) × 10$^{12}$ |
| 4 | 5.0 | 60 | 8818±94 | 4.0 (±0.04) × 10$^{12}$ |
| 5 | 10.0 | 60 | 7064±84 | 3.2 (±0.04) × 10$^{12}$ |
| 6 | 32.5 | 60 | 7627±87 | 3.4 (±0.04) × 10$^{12}$ |
| 7 | 60.0 | 60 | 8491±92 | 3.8 (±0.04) × 10$^{12}$ |
| 8 | 120.0 | 60 | 12627±112 | 5.7 (±0.05) × 10$^{12}$ |
| 9 | 240.0 | 60 | 11418±107 | 5.2 (±0.04) × 10$^{12}$ |
| 10 | 1313.0 | 60 | 9764±99 | 4.4 (±0.04) × 10$^{12}$ |

[a]The intensity is obtained by totaling the number of counts in a circle of area 0.11 cm$^2$.
[b]Calculated by comparing the number of photostimulated luminescence counts measured on the gold substrates to a radio-image obtained of a spot of $^{32}$P radiolabeled DNA of known concentration.
[c]MCH control sample.

Fig. 6

SURFACE IMMOBILIZATION OF BIOPOLYMERS

RELATED APPLICATIONS

The present application is based on U.S. Provisional Patent Application No. 60/033,042 filed Dec. 11, 1996, the entire disclosure and contents of which is hereby incorporated by reference.

BACKGROUND OF THE INVENTION

1. Field of the Invention

The present invention relates generally to biopolymer probes immobilized on the surface of a substrate.

2. Description of the Prior Art

New methods for genetic screening and sequencing are based on the hybridization of surface immobilized single-stranded oligonucleotides, or DNA probes. Thiol-derivatized, single-stranded DNA has been used to model hybridization reactions at surfaces. For example, Lee et al. have described covalently attaching thiolated DNA to derivatized silane layers on silica for use in atomic force microscopy studies (Lee et al., "Direct Measurement" in *Science*, (1994), 266, 771–773). Okahata et al. have prepared a monolayer consisting of thiol-derivatized DNA 10-mers on gold, and measured the mass changes during hybridization using a quartz crystal microbalance (Okahata et al., "Hybridization of Nucleic Acids Immobilized on a Quartz Crystal Microbalance" in *J. Amer. Chem. Soc.*, (1992), 114, 8299–8300). Leavitt et al. describe modifying the phosphate group of the nucleotide backbone with a sulfur group which is adsorbed directly on the surface (Leavitt et al., "Angle-Dependent X-ray Photoelectron Spectroscopy and Atomic Force Microscopy of Sulfur-Modified DNA on Au(111)" in *J. Phys. Chem.*, (1994), 98, 8742–8746).

A problem with all of these prior methods is that is that the DNA can interact strongly with the gold surface, resulting in probes with low hybridization activity. In addition, the prior methods do not permit facile control of the surface coverage of DNA probes.

SUMMARY OF THE INVENTION

The surface-confined biopolymers of the present invention differ from prior oligonucleotide probes in that the surface coverage of the thiol-derivatized biopolymers of the present invention can be precisely controlled by creating mixed monolayers of thiol-derivatized probes and a diluent thiol such as mercaptohexanol. Because it has been discovered that controlling the surface coverage of thiol-derivatized DNA on a gold surface can maximize the hybridization efficiency of surface-bound probes, the present invention is more useful for specific hybridization of single-stranded DNA and other nucleotides than prior immobilization strategies.

In one embodiment, the present invention provides a biopolymer-containing monolayer comprising thiol-derivatized biopolymers and organic thiols bound to a metal substrate. Preferably, the biopolymers are oligonucleotides and are most preferably single-stranded DNA probes.

In another embodiment, the present invention provides a method for forming a biopolymer-containing monolayer comprising the steps of: applying thiol-derivatized biopolymers to a metal substrate to bind the thiol-derivatized biopolymers thereto; and applying an organic thiol to the substrate to bind the organic thiol to the substrate, to remove nonspecifically bound biopolymers and to passivate the surface, preventing adsorption of target biopolymers from solution. In addition, passivation of the surface with a diluent thiol increases the biological activity of the immobilized biopolymers. Preferably, the biopolymer is an oligonucleotide and most preferably is single-stranded DNA.

Particularly with respect to oligonucleotides, the present invention has advantages over prior immobilization strategies in that precise control can be achieved over the coverage of the thiol-derivatized, single-stranded oligonucleotides on metal surfaces. Also, the surface-immobilized oligonucleotide retains high activity and specificity for hybridization with the complementary sequence as a result of posttreatment with the diluent thiol. In addition, very little, if any, oligonucleotide from solution adsorbs nonspecifically on the two component monolayer.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 6 is a table (Table 1) which contains data obtained from radioimages of HS-ssDNA/MCH monolayers exposed to $^{32}$P-radiolabeled complement.

DETAILED DESCRIPTION OF THE PREFERRED EMBODIMENT

Definitions

Figure 1:
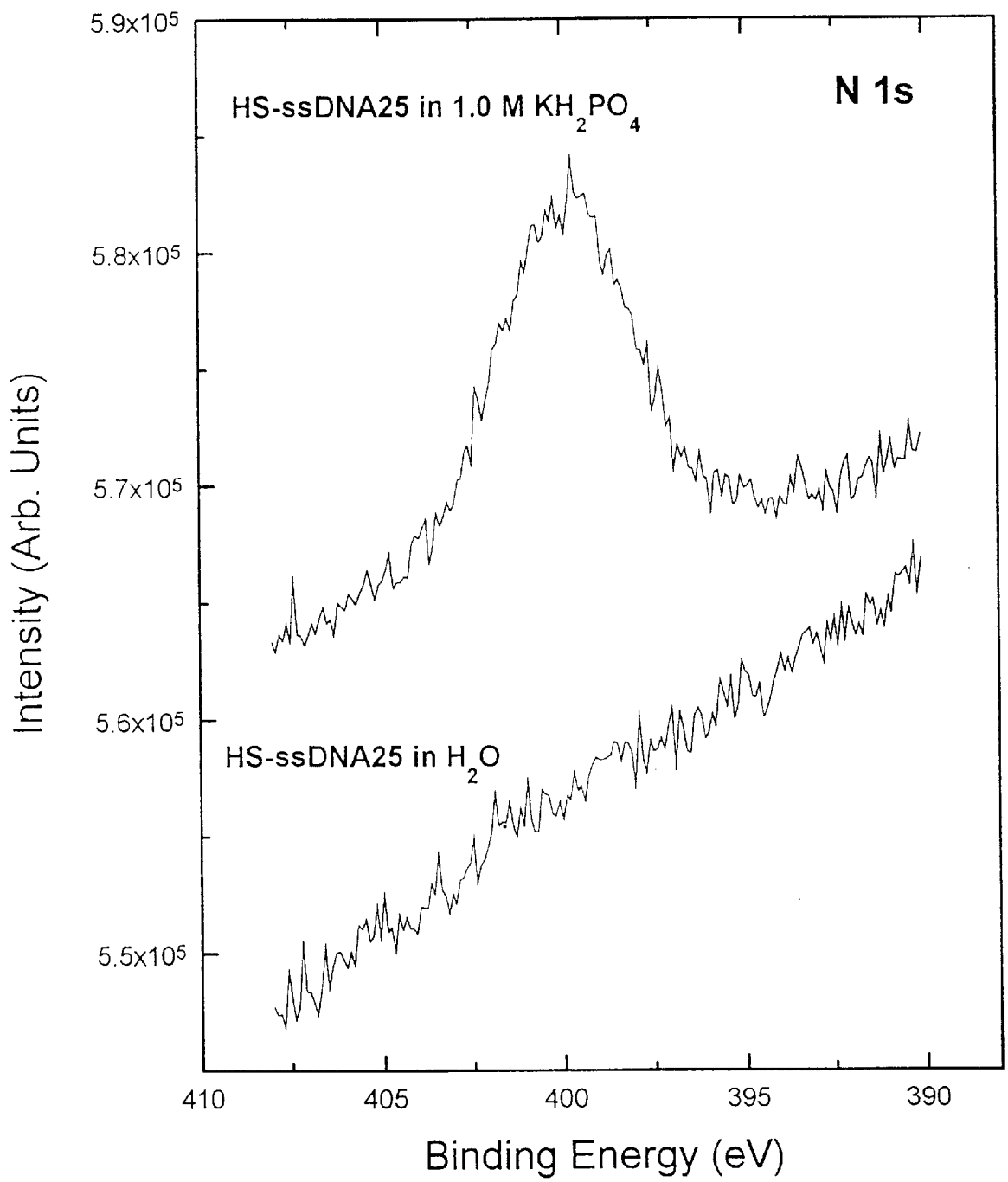
FIG. 1 is a graph of XPS N 1s data obtained from 1.0 $\mu$M HS-ssDNA in pure water and in 1.0 M in $KH_2PO_4$.

For the purposes of the present invention, the term "oligonucleotide" refers to any oligonucleotide, including double and single-stranded DNA, RNA, PNAs (peptide nucleic acids) and any sequence of nucleic acids, either natural or synthetic, derivatized or underivatized.

For the purposes of the present invention, the term "HS-ssDNA" refers to a thiol-derivatized single-stranded DNA probe.

For the purposes of the present invention, the term "biopolymer" refers to any oligonucleotide, polypeptide, polysaccharide, and derivatives thereof.

For the purposes of the present invention, the term "organic linker" refers broadly to an a organic chain which links a thiol group to a biopolymer. The organic chain may be saturated or unsaturated, may include aryl groups, may include alkyl, alkenyl, or aryl side chains, and may include one or more functional groups such as ether groups, hydroxy groups, carboxy groups, halide groups, etc.

Description

The probes of the present invention can be formed using any biopolymer which can be derivatized with a thiol and bound to a metal substrate through the sulfur atom of the thiol. The probes of the present invention are preferably formed from oligonucleotides. Most preferably the probes of the present invention are formed from single-stranded DNA (ssDNA) which have been reacted with a thiol to form thiol-derivatized DNA (HS-ssDNA).

The hybridization activity of surface-bound HS-ssDNA is dependent on surface coverage. One method of varying the surface coverage is to control the ionic strength of the HS-ssDNA solution. Another method to control coverage is to vary the immersion time in the HS-ssDNA solution. A primary advantage of the surface-bound probes of the present invention is that nonspecifically adsorbed DNA is largely removed from the surface. Thus, the majority of surface bound probes are accessible for specific hybridization with complementary oligonucleotides and can discriminate between complementary and non-complementary target molecules. Moreover, the surface-bound probes of the present invention are stable, and can survive temperature cycling and exposure to air.

The probes of the present invention are preferably bound to a gold substrate. However, preferred metal substrates also include other noble metals, such as: silver, copper, platinum, palladium, ruthenium, and iridium to which thiols readily attach through the sulfur atom. Alloys of these metals may also be used as a substrate in the present invention.

The diluent thiol used in the present invention serves two roles: it removes nonspecifically bound HS-ssDNA, and it prevents nonspecific adsorption of oligonucleotides from solution. Specifically, the hydroxyl group functionality of the diluent thiol prevents nonspecific adsorption of DNA from solution. It is possible that thiols including functional groups other than a hydroxyl group may also be effective in preventing nonspecific adsorption of DNA from solution. Therefore, although hydroxy-terminated organic thiols such as mercaptohexanol are preferred thiols, it is contemplated that other suitable thiols that prevent nonspecific adsorption may be used for the purposes of the present invention. Furthermore, it is contemplated that diluent thiols having both a shorter and longer chain length than mercaptohexanol could be used for the purposes of the invention. Such diluent thiols may include thiols having saturated or unsaturated carbon chains, having aryl groups as part of the carbon chain, having side chains, having ether linkages, etc.

The biopolymer is preferably derivatized so that an organic linker, such as a hexamethylene linker ($-(CH_2)_6$), acts as a spacer group to separate the biopolymer from the thiol (—SH) group. When the biopolymer is ssDNA, the presence of this organic linker/spacer group in the HS-ssDNA allows all of the nucleotides of the ssDNA to be available for hybridization. However, the present invention also contemplates that the biopolymer, such as ssDNA, could be directly bound to the thiol group. In this situation, some of the ssDNA nucleotides would be used as the spacer group with the balance available for hybridization.

Although HS-ssDNA is a preferred thiol-derivatized oligonucleotide for the present invention, it is contemplated that oligonucleotide monolayers could be formed using thiol-derivatized RNA, PNAs and other modified and un-modified oligonucleotides which are used for hybridization reactions.

The invention will now be described by way of example. The following example is illustrative and is not meant to limit the scope of the invention which is set forth by the appointed claims.

EXAMPLE

Single-crystal (100) silicon wafers were used as substrates in the preparation of evaporated Au films. The Au thin films were prepared by thermal evaporation of 200 nm of Au over a 10 nm Cr adhesion layer. The Au substrates were cleaned in piranha solution (70% $H_2SO_4$: 30% $H_2O_2$) before exposure to the sample solutions.

The thiolated single-stranded DNA, abbreviated HS-ssDNA25, is a 25-base oligonucleotide with the following sequence: 5'-HS-$(CH_2)_6$-CAC GAC GTT GTA AAA CGA CGG CCA G-3'. The complementary single-stranded DNA is a 25-mer with the sequence 5'-CTG GCC GTC GTT TTA CAA CGT CGT G-3', abbreviated ssDNA-C25. The non-complementary control has the same sequence as the immobilized probe, 5'-CAC GAC GTT GTA AAA CGA CGG CCA G-3', without the HS-$(CH_2)_6$ attachment.

Figure 4A:
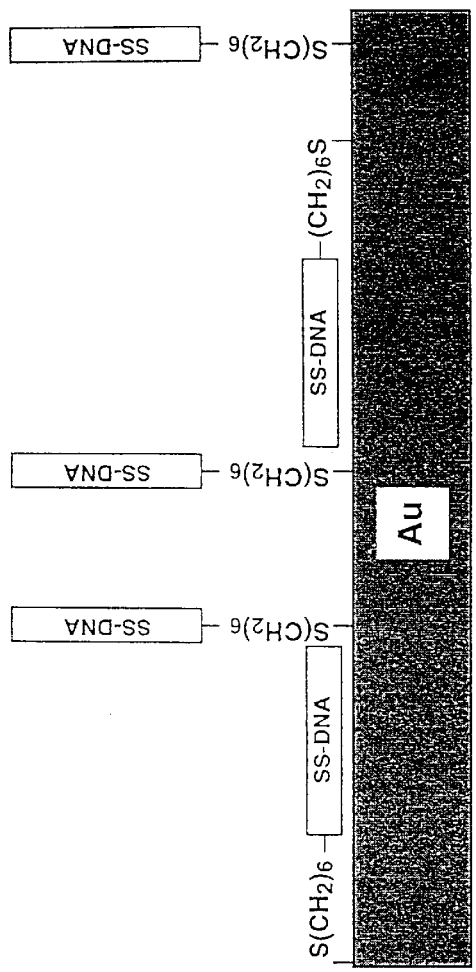
FIG. 4A is a schematic diagram of a HS-ssDNA/MCH monolayer before posttreatment with MCH.
Figure 4B:
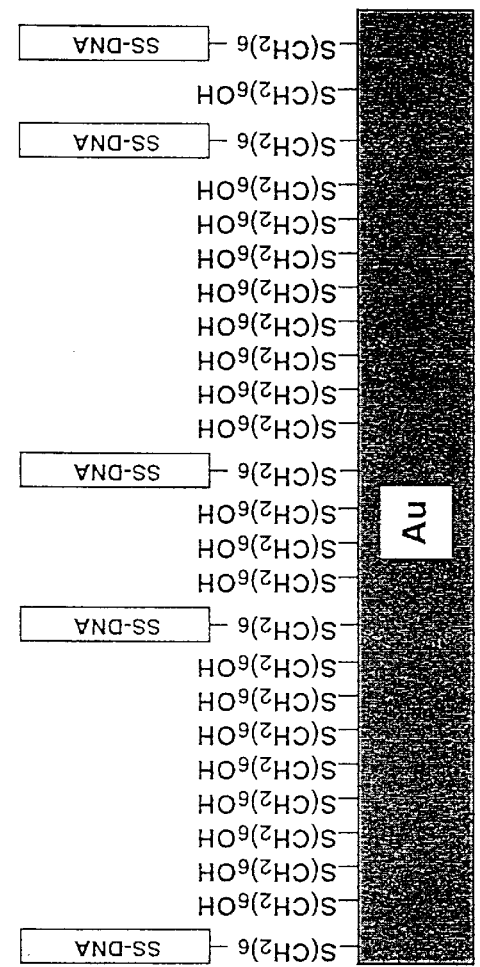
FIG. 4B is a schematic diagram of a HS-ssDNA/MCH monolayer after posttreatment with MCH.

HS-ssDNA25 surfaces were prepared by placing piranha-cleaned Au in $KH_2PO_4$ buffer solutions of DNA. The $KH_2PO_4$ solution concentration was 1.0 M unless otherwise stated. Mixed monolayer surfaces containing HS-ssDNA25 and mercaptohexanol (MCH) were prepared by immersing the clean gold substrate in a 1.0 $\mu$M solution of HS-ssDNA25 for 15 seconds to 22 hours, followed by a one hour exposure of the sample to an aqueous solution of 1.0 mM MCH. Before analysis or hybridization, each sample was rinsed thoroughly with deionized water. FIG. 4A shows, in schematic form, the HS-ssDNA/MCH monolayer before posttreatment with MCH and FIG. 4B shows, in schematic form, the HS-ssDNA/MCH monolayer after posttreatment with MCH.

Hybridization of the HS-ssDNA25 immobilized on gold was measured using $^{32}P$ radiolabeling. Complementary and non-complementary DNA oligonucleotides were radiolabeled with $^{32}P$ using T4 polynucleotide kinase and gamma $^{32}P$ ATP (30000 Ci/mmole). Hybridization was done at 24°0 C. for 90 minutes in TE-1M NaCl (10 mM Tris-HCl, 1 mM EDTA, 1 M NaCl). After hybridization, samples were rinsed in 1 mL of TE eight times, ten seconds each rinse. Samples were air-dried before imaging. Hybridization of the surface bound probe with its complement was monitored by obtaining radio-images using a photostimulatable storage imaging plate system. The imaging instrument is capable of 100 $\mu$M spatial resolution.

Figure 2:
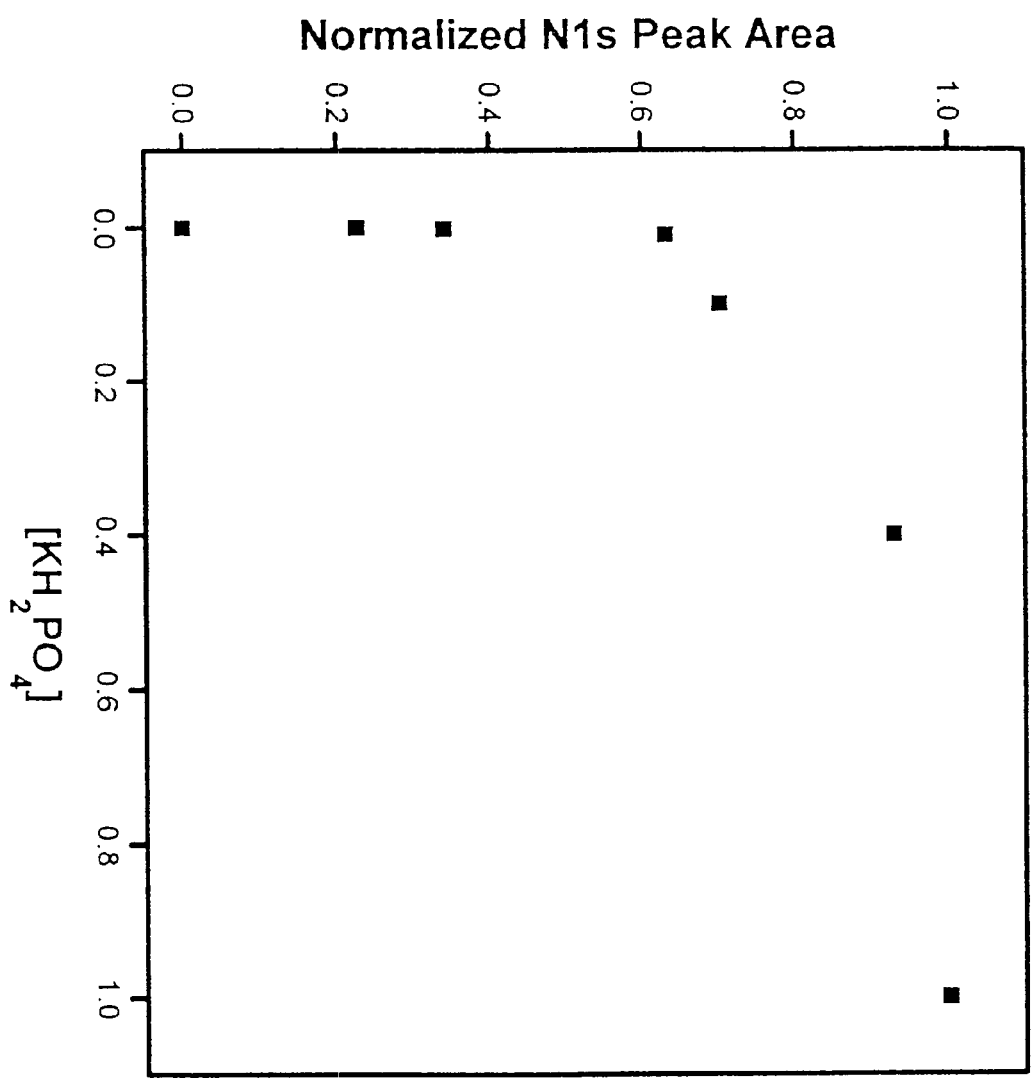
FIG. 2 is a graph of normalized XPS N 1s peak areas plotted as a function of ionic strength of the 1.0 $\mu$M HS-ssDNA solution.

The amount of HS-ssDNA25 adsorbed on the surface was monitored by measuring the XPS N 1s signal. The inventors have found that the presence of the N 1s peak in the XPS data is a reliable indication that DNA is adsorbed on the surface. Bare gold samples exposed to air or buffer solutions containing no DNA exhibit no-XPS-detectable nitrogen. Therefore, any observed N signal originated exclusively from the nitrogen containing purine and pyrimidine bases of DNA. Furthermore, the relative amounts of adsorbed DNA for different samples was determined by comparison of N 1s peak areas. Shown in FIG. 1 are XPS data obtained from samples immersed in 1.0 $\mu$M HS-ssDNA25 solutions, prepared either in pure water or in 1.0 M $KH_2PO_4$ buffer. For the HS-ssDNA25 solution prepared in pure water, essentially no N 1s peak is observed, indicating that HS-ssDNA dissolved in water does not adsorb on gold. By contrast, a relatively intense N 1s peak is observed when a sample is exposed to an identical HS-ssDNA sequence prepared in 1.0 M $KH_2PO_4$ buffer. To explore further the role of ionic strength on adsorption of HS-ssDNA, XPS data were obtained from a series of samples exposed to 1.0 $\mu$M HS-ssDNA25 solutions prepared in different concentrations of $KH_2PO_4$ buffer. Normalized N 1s peak areas obtained from this series of solutions plotted as a function of $KH_2PO_4$ concentration are displayed in FIG. 2. The XPS N 1s peak area for buffer concentrations of $2.7 \times 10^{-4}$ to 1.0 M $KH_2PO_4$ grows five-fold as the buffer concentration is increased, evidence that ionic strength plays a critical role in adsorption of DNA.

After determining from these XPS studies that the surface coverage obtained for the HS-ssDNA in 1.0 M $KH_2PO_4$ was maximized, an attempt was made to hybridize the surface-bound probe with its radiolabeled complement, ssDNA-C25. Hybridization was measured by obtaining radio images of the HS-ssDNA25 sample after exposing it to the radiolabeled complement. No signal from the radiolabel was measured, indicating that hybridization did not occur. It is believed that hybridization on this surface is inhibited due to steric and electrostatic factors. The complement cannot access the surface-bound HS-ssDNA25, as the molecules on the surface are too tightly packed. The dense packing of these charged groups on the surface may also prohibit the approach and binding of another similarly charged DNA molecule.

Figure 3:
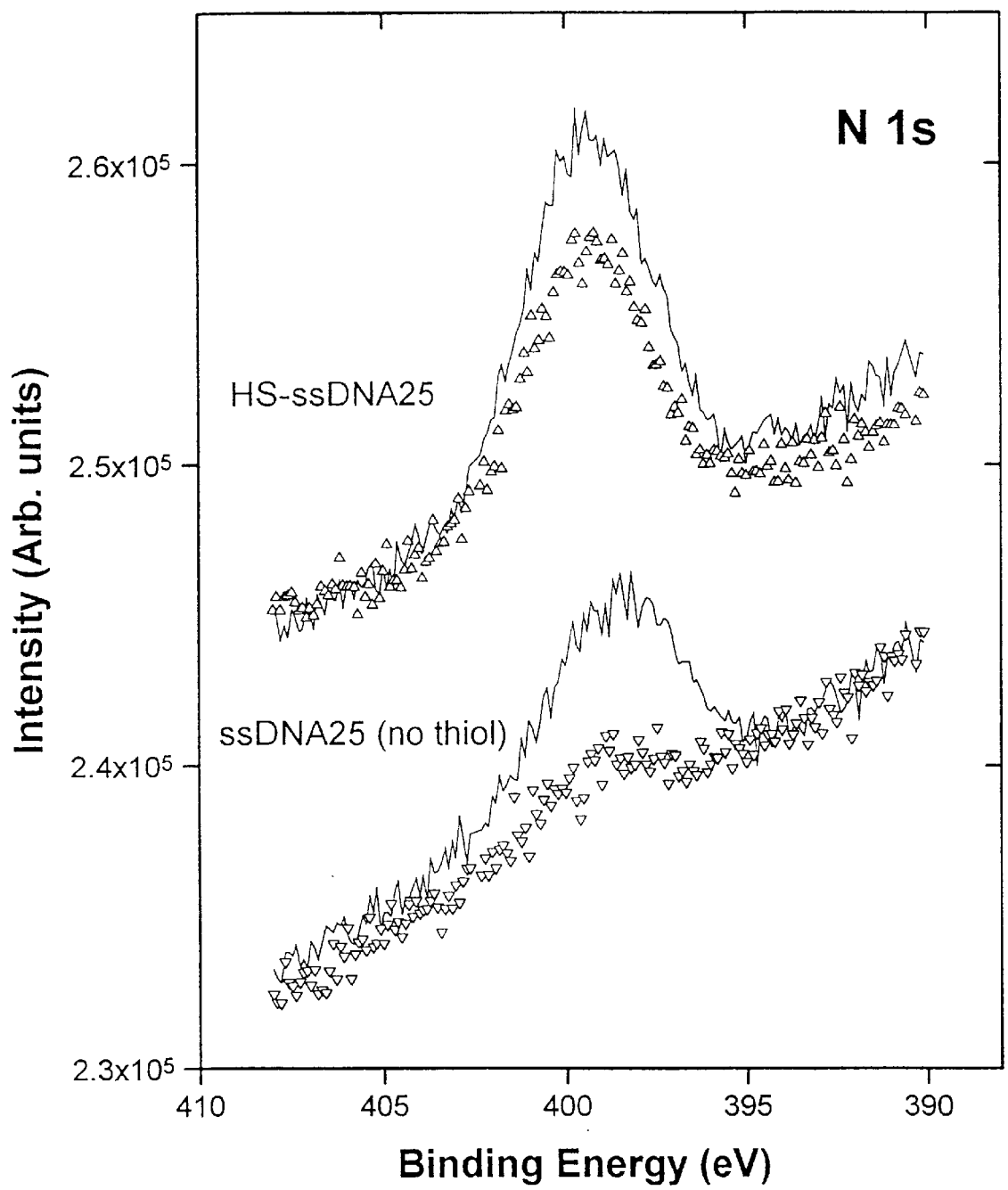
FIG. 3 shows the XPS N 1s spectra of thiol-derivatized and non-thiol derivatized ssDNA before (solid lines) and after (triangles) exposure to MCH.

To determine whether HS-ssDNA25 is adsorbed on the gold surface "specifically" through the sulfur atom or "non-specifically" through the nitrogen-containing nucleotide side chains interacting directly with the surface, or some other functionality of the DNA, XPS data from the thiol-derivatized DNA (HSssDNA25) and the non-thiol derivatized DNA (ssDNA25) were obtained and compared. The XPS N 1s data for HS-ssDNA and the ssDNA are shown in FIG. 3. The N 1s peak area of the non-thiol derivatized DNA is approximately 50 to 60% of the intensity measured for adsorbed HS-ssDNA, indicating that more DNA is adsorbed when the molecule is thiol-derivatized. There is a significant amount of DNA adsorption for the non-derivatized oligonucleotide, suggesting that DNA will interact with and adsorb on the surface when no thiol group is present. The non-derivatized DNA is adsorbed strongly on the surface; heating the gold surface exposed to non-thiol-derivatized ssDNA25 to 75° C. did not cause desorption of ssDNA25. None intensity of the N 1s signal for HS-ssDNA is evidence that the strong thiol-gold interaction drives the adsorption of HS-ssDNA25 to higher coverages, compared to the non-thiolated DNA.

As a means of measuring how tightly the HS-ssDNA25 and non-thiolated ssDNA25 monolayers are bound to the surface, both HS-ssDNA25 (thiolated) and ssDNA (non-thiolated) surfaces were exposed to another thiol, mercaptohexanol (MCH), for one hour. The XPS N 1s data obtained after posttreatment with MCH for both HS-ssDNA and ssDNA samples are shown in the scatter plots in FIG. 3, along with the XPS data obtained before MCH exposure. It is clear that both HS-ssDNA25 and non-thiolated ssDNA25 coverages are altered by posttreatment with MCH. The N 1s peak obtained from the HS-ssDNA25 sample is slightly less intense than that observed before exposure to MCH, indicating that a small amount of HS-ssDNA has been removed or displaced form the surface. A much more dramatic difference between the "before" and "after" XPS data for non-thiolated ssDNA25 is observed. Essentially all of the non-thiolated DNA is removed from the surface, presumably displaced by MCH. The significance of this result is three-fold: First, it is clear that the HS-ssDNA25 is adsorbed through the sulfur atom, as the HS-ssDNA25 is not displaced by MCH posttreatment, but the non-thiolated ssDNA25 is almost completely removed. Second, posttreatment with MCH results in removal of nonspecifically bound, single-stranded DNA. Third, the HS-ssDNA25 molecules remaining on the surface after MCH treatment are raised off the surface, tethered by the sulfur group.

Mixed HS-ssDNA/MCH monolayers of varying coverage were formed by a two step process. First, clean bare gold was immersed in a 1.0μM HS-ssDNA25 solution in 1.0 M $KH_2PO_4$ for a specific amount of time (referred to here as "exposure time"), followed by rinsing with water. Second, the HS-ssDNA25-treated surface was exposed to a 1.0 mM aqueous solution of MCH for exactly one hour.

MCH was used for three reasons: First, and, perhaps, most importantly, nonspecific binding of DNA on a self-assembled monolayer (SAM) of MCH does not occur. That is, if a pure MCH monolayer is formed, DNA will not adsorb on the hydroxy-terminated surface of the MCH monolayer. Second, MCH is soluble in aqueous solutions. Third, the 6 carbon chain of MCH is the same length as the methylene spacer in HS-ssDNA.

Figure 5:
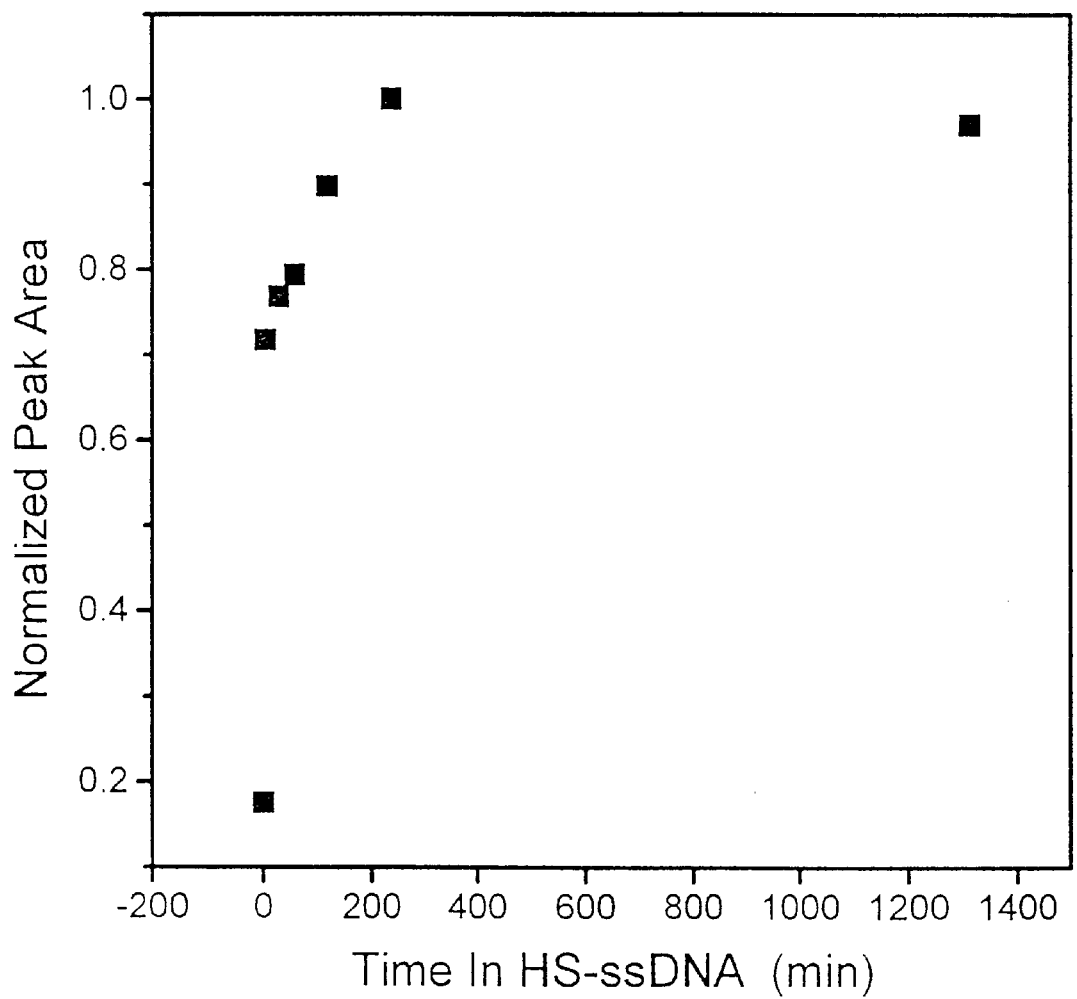
FIG. 5 is a graph of normalized N 1s peak areas plotted as a function of sample exposure time to HS-ssDNA.

A series of HS-ssDNA25/MCH surfaces were prepared by the above method, with exposure times ranging from 1 minute to 21.9 hours. The relative amount of HS-ssDNA on the surface was determined by measuring the XPS N 1s peak areas. Shown in FIG. 5 are the normalized N 1s peak areas plotted as a function of time in the HS-ssDNA solution. The N 1s peak intensity is observed to increase monotonically with exposure time. The amount of HS-ssDNA25 on the surface appears to reach a maximum at 240 minutes; the sample that had been exposed to HS-ssDNA25 for 21.9 hours does not have more DNA on the surface than the sample exposed for 240 minutes.

In order to measure the optimal HS-ssDNA25 coverage for hybridization, a series of surfaces with varying HS-ssDNA25 coverages in an HS-ssDNA25/MCH mixed monolayer were exposed to $^{32}P$-radiolabeled complement. Each surface was exposed to a separate hybridization solution containing the radiolabeled complement for 90 minutes and then rinsed in TE buffer. The results from this experiment are summarized in Table 1 of FIG. 6, along with results obtained from exposing both a bare gold sample and a pure MCH monolayer to the radiolabeled complement. The bare gold and pure MCH samples served as controls which monitored nonspecific adsorption. All of these surfaces were subjected to the same hybridization protocol with the $^{32}P$ radiolabeled complement, ssDNA-C25. In addition, a second set of identically prepared surfaces was exposed to a different radiolabeled oligonucleotide that was not complementary to the surface bound probe. This set of samples was used to estimate any nonspecific binding of the radiolabeled probe to the surface as well as nonspecific hybridization between mismatched oligonucleotides.

Hybridization or adsorption of the complement on the HS-ssDNA25-coated substrates and the control samples was uniform, without any indication of bare patches or clumping of radiolabeled oligonucleotides. The control sample of the pure MCH monolayer shows negligible adsorption of the radiolabeled target. By contrast, the bare gold substrate has a significant amount of the radiolabeled complement adsorbed. For the HS-ssDNA25/MCH coated surfaces, hybridization is evidenced by the binding of the radiolabeled probe to the substrate. As the HS-ssDNA coverage increases, more of the radiolabeled probe is observed on the surfaces. Hybridization was greatest for sample 8, which corresponds to an exposure time of 120 minutes. It is interesting to note that the most hybridization is not observed for the highest HS-ssDNA25 coverage samples (samples 9 and 10). In fact, for exposure times longer than 120 minutes, a decrease in hybridization efficiency is observed (defined for the purposes of the present invention as the product of the total number of surface bound probes and the percentage of probes undergoing hybridization), as evidenced by the decrease in the amount of radiolabeled probe measured at the surface. It is believed that the decrease in the number of duplexes formed on the surface for higher coverage samples (samples 9 and 10) is due to steric and electrostatic hindrance arising from the more tightly packed DNA monolayer, as described earlier.

It is clear from the hybridization experiment that the HS-ssDNA25 appears to be uniformly distributed on the surfaces, and that the optimal surface coverage for hybridization for the samples examined is that obtained for the 120 minute HS-ssDNA exposure time sample. The hybridization efficiency on this surface can be estimated by comparing the number of counts in a known volume of radiolabeled DNA that has been spotted on the paper and exposed to the imaging plate. It appears that there are $5.7\ (\pm 0.05) \times 10^{12}$ molecules/cm² of the radiolabeled probe bound to sample 8. From independent measurement of the HS-ssDNA coverage using surface plasmon resonance, the hybridization efficiency is estimated to be close to 100%.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A biopolymer-containing monolayer comprising:
   a metal substrate;
   a plurality of thiol-derivatized oligonucleotides bound to said substrate by a sulfur-substrate linkage, said thiol-derivatized oligonucleotides having the formula:

HS—X—Y where
   X is either nothing or an organic linker, and
   Y comprises an oligonucleotide terminally bound to X where X is an organic linker or terminally bound to S where X is nothing; and
   a plurality of organic thiols bound to said substrate, wherein said plurality of bound thiol-derivatized boligonucleotides and said plurality of bound organic thiols comprise a mixed monolayer.

2. The biopolymer-containing monolayer of claim 1, wherein said thiol-derivatized oligonucleotide comprise thiol-derivatized single-stranded DNA.

3. The biopolymer-containing monolayer of claim 1, wherein said thiol-derivatized oligonucleotides comprise RNA.

4. The biopolymer-containing monolayer of claim 1, wherein said thiol-derivatized oligonucleotides comprise PNA.

5. The biopolymer-containing monolayer of claim 1, wherein Y is a nucleotide sequence of at least six nucleotides.

6. The biopolymer of claim 1, wherein X comprises an organic linker.

7. The biopolymer-containing monolayer of claim 1, wherein said metal substrate comprises a metal selected from the group consisting of the metals gold, silver, platinum, palladium, ruthenium and iridium and alloys of said metals.

8. The biopolymer-containing monolayer of claim 1, wherein said substrate comprises gold.

9. The biopolymer-containing monolayer of claim 1, wherein said organic thiol includes a terminal hydroxy group.

10. The biopolymer-containing monolayer of claim 1, wherein X comprises a hexamethylene linker and said organic thiol compound comprises mercaptohexanol.

11. A method for forming a biopolymer-containing monolayer comprising the steps of:
    applying a solution comprising thiol-derivatized oligonucleotides to a substrate comprising a metal to bind said thiol-derivatized oligonucleotides thereto by a sulfur-substrate linkage, the thiol-derivatized oligonucleotides having the formula:

HS—X—Y where
    X is either nothing or an organic linker; and
    Y comprises an oligonucleotide terminally bound to X where X is an organic linker or terminally bound S where X is nothing; and
    applying a solution comprising an organic thiol to displace nonspecifically adsorbed oligonucleotides and to prevent nonspecific adsorption of oligonucleotides.

12. The method of claim 11, further comprising rinsing the substrate to which the thiol-derivatized oligonucleotides and the thiols are bound with water to remove compounds not bound to the substrate.

13. The method of claim 11, wherein said thiol-derivatized oligonucleotides comprise thiol-derivatized single-stranded DNA.

14. The method of claim 11, wherein said thiol-derivatized oligonucleotides comprise RNA.

15. The method of claim 11, wherein said thiol-derivatized oligonucleotides comprise PNA.

16. The method of claim 11, wherein Y is a nucleotide sequence of at least six nucleotides.

17. The method of claim 11, wherein the organic thiol is applied to the substrate by immersing the substrate in an aqueous solution of the organic thiol, thereby removing nonspecifically adsorbed thiol-derivatized oligonucleotides and passivating the surface against nonspecific adsorption of oligonucleotides in solution.

18. The method of claim 11, wherein X comprises an organic linker.

19. The method of claim 11, wherein the substrate comprises a metal selected from the group consisting of the metals gold, silver, platinum, palladium, iridium and ruthenium and alloys of said metals.

20. The method of claim 11, wherein the substrate comprises gold.

21. The method of claim 11, wherein the organic thiol includes a terminal hydroxy group.

22. The method of claim 11, wherein X comprises a hexamethylene linker and said organic thiol comprises mercaptohexanol.

* * * * *